US006431864B1

(12) United States Patent
Silverstein

(10) Patent No.: US 6,431,864 B1
(45) Date of Patent: Aug. 13, 2002

(54) DENTAL TOOL

(76) Inventor: Harry P. Silverstein, 1725 Lombard St., Philadelphia, PA (US) 19146

( * ) Notice: Subject to any disclaimer, the term of this patent is extended or adjusted under 35 U.S.C. 154(b) by 0 days.

(21) Appl. No.: 09/803,220

(22) Filed: Mar. 9, 2001

(51) Int. Cl.$^7$ ................................................ A61C 3/14
(52) U.S. Cl. ....................................................... 433/159
(58) Field of Search ................................ 433/159, 160, 433/161, 162; 606/210, 211; 294/99.2, 33; 968/666, DIG. 1

(56) References Cited

U.S. PATENT DOCUMENTS

| | | | |
|---|---|---|---|
| 421,925 A | | 2/1890 | Graves |
| 468,746 A | | 2/1892 | How |
| 740,549 A | | 10/1903 | Gilbert |
| 1,033,942 A | | 7/1912 | Ruggles |
| 1,198,958 A | | 9/1916 | Risley |
| 1,386,436 A | | 8/1921 | Smith |
| 1,439,022 A | | 12/1922 | Quilling |
| 1,537,793 A | | 5/1925 | Bates |
| 1,758,490 A | | 5/1930 | Aderer |
| 1,886,127 A | | 11/1932 | Silvis |
| 3,741,602 A | * | 6/1973 | Ploeckelmann ............. 606/210 |
| 3,972,333 A | | 8/1976 | Leveen ........................ 128/318 |
| 4,001,940 A | | 1/1977 | Cusato |
| 4,873,979 A | | 10/1989 | Hanna ......................... 128/354 |
| 4,888,015 A | | 12/1989 | Domino ......................... 623/6 |
| 5,047,037 A | | 9/1991 | Brandfield ................... 606/138 |
| 5,047,049 A | * | 9/1991 | Salai ........................... 606/211 |
| 5,472,450 A | | 12/1995 | Mena ........................ 606/205 |
| 6,095,815 A | * | 8/2000 | Mueller ....................... 433/159 |
| 6,322,363 B1 | * | 11/2001 | Beecher et al. ............. 433/159 |

* cited by examiner

Primary Examiner—Cary E. O'Connor
(74) Attorney, Agent, or Firm—Morgan, Lewis & Bockius, LLP

(57) ABSTRACT

A method of placing an object having a substantially planar surface into a channel between a pair of teeth, implemented by a grasping tool, including providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, applying pressure on the first pressure portion and the second pressure portion simultaneously to grasp the object, moving the dental tool and the object toward the channel, inserting the object into the channel, and releasing the pressure from the first pressure portion and the second pressure portion to free the object from the dental tool; the first end affixed to the second end to form a base, the first tip and the second tip substantially oblique to a plane passing through the base, and the first surface of the first arm opposite the first surface of the second arm. The grasping tool including a first arm having an angled first tip, a first end opposite the angled first tip, a first surface, and a second surface opposite the first surface, a second arm having an angled second tip, a second end opposite the angled second tip, a first surface, and a second surface opposite the first surface, where the second end is affixed to the first end to form a base, the second surface of the first arm faces the second surface of the second arm, a plane passing through the base between the first arm and the second arm, a pin mounted on the second surface of the first arm, an opening through the second arm that receives the pin, a first pressure portion on the first surface of the first arm, a second pressure portion on the first surface of the second arm, a first mating portion on the second surface of the first arm and opposite the first pressure portion, and a second mating portion on the second surface of the second arm and opposite the second pressure portion; the first angled tip and the angled second tip substantially oblique to the plane passing through the base while the tool is in a closed position, a portion of the angled first tip and a portion of the angled second tip mating when the tool is in a closed position such that the pin engages the opening, and the second mating portion contiguous with the first mating portion when a maximum pressure is applied to the first pressure portion and the second pressure portion.

12 Claims, 2 Drawing Sheets

DENTAL TOOL

FIELD OF THE INVENTION

This invention relates to the field of dental and medical instruments and in particular to a dental tool for grasping planar objects.

BACKGROUND OF THE INVENTION

Dental instruments may be used to place and remove objects into and from an individual's mouth. It may be necessary for a dentist to place the objects between a pair of teeth to correct or repair the individual's teeth, and it may be necessary to remove the objects after the dental work is performed. It is believed that current dental instruments that hold these objects are difficult to maneuver, especially when inserted into the back of the individual's mouth. This may cause discomfort for the individual and frustration for the dentist.

A dental instrument used to place objects into and remove objects from an individual's mouth is shown in FIG. 1. The instrument 1 has a first arm 2 and a second arm 3. An object is held between the tips 4 and 5 of the first and second arms 2 and 3, respectively such that as the instrument 1 picks up the object, a locking mechanism 6 on the first arm 2 engages a void 7 within the second arm 3. A pin 8 on the first arm 2 also engages an opening 9 in the Sex second arm 3 to align the first arm 2 with the second arm 3. The locking mechanism 6 allows the tips 4 and 5 to hold the object in place until the locking mechanism 6 is manually released from the void 7.

SUMMARY OF THE INVENTION

The present invention provides a method of placing an object having a substantially planar surface into a channel between a pair of teeth. The method includes providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, applying pressure on the first pressure portion and the second pressure portion simultaneously to grasp the object, moving the dental tool and the object toward the channel, inserting the object into the channel, and releasing the pressure from the first pressure portion and the second pressure portion to free the object from the dental tool. The first end is affixed to the second end to form a base, the first tip and the second tip are substantially oblique to a plane passing through the base, and the first surface of the first arm is opposite the first surface of the second arm.

The present invention also provides another method of placing an object having a substantially planar surface into a channel between a pair of teeth. This method includes providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, picking up the dental tool, holding the dental tool at the first pressure portion and the second pressure portion, applying pressure on the first pressure portion and the second pressure portion simultaneously, moving the first arm and the second arm at substantially the same distance toward the plane, inserting the pin into the opening to align the first arm with the second arm, and grasping the object with the first tip and the second tip such that a line passing through a center of the object is perpendicular to the plane. This method further includes moving the dental tool and the object toward the channel, entering a mouth such that the first arm and the second arm are substantially oblique to a line passing through each center of the pair of teeth and the channel, inserting the object into the channel, and releasing the pressure from the first pressure portion and the second pressure portion to free the object from the dental tool. The first end is affixed to the second end to form a base, the first tip and the second tip are substantially oblique to a plane passing through the base, and the first surface of the first arm is opposite the first surface of the second arm.

The present invention further provides a method of dislodging an object having a substantially planar surface from a channel between a pair of teeth. This method includes providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, applying pressure on the first pressure portion and the second pressure portion simultaneously to grasp the object, removing the object from the channel, moving the dental tool and the object away from the channel, and releasing the pressure from the first pressure portion and the second pressure portion to free the object from the dental tool. The first end is affixed to the second end to form a base, the first tip and the second tip are substantially oblique to a plane passing through the base, and the first surface of the first arm is opposite the first surface of the second arm.

The present invention also provides a grasping tool. The grasping tool includes a first arm having an angled first tip, a first end opposite the angled first tip, a first surface, and a second surface opposite the first surface, a second arm having an angled second tip, a second end opposite the angled second tip, a first surface, and a second surface opposite the first surface, where the second end is affixed to the first end to form a base and the second surface of the first arm faces the second surface of the second arm, a plane pass or through the base between the first arm and the second arm, a pin mounted on the second surface of the first arm, and an opening through the second arm that receives the pin. The grasping tool also includes a first pressure portion on the first surface of the first arm, a second pressure portion on the first surface of the second arm, a first mating portion on the second surface of the first arm and opposite the first pressure portion, and a second mating portion on the second surface of the second arm and opposite the second pressure portion. The angled first tip and the angled second tip are substantially oblique to the plane passing through the base while the tool is in a closed position, and a portion of the angled first tip and a portion of the angled second tip mate when the tool is in a closed position such that the pin engages the opening. The second mating portion is contiguous with the first mating portion when a maximum pressure is applied to the first pressure portion and the second pressure portion.

The present invention further provides a dental tool. The dental tool includes a first arm having an angled and substantially planar first tip, a first end opposite the angled first tip, a first surface, and a second surface opposite the first surface, a second arm having an angled and substantially planar second tip, a second end opposite the angled second tip, a first surface, and a second surface opposite the first surface. The second end is affixed to the first end by a weld to form a base and the second surface of the first arm faces the second surface of the second arm. The dental tool also includes a plane passing through the base between the first arm and the second arm, where the angled first tip and the angled second tip are substantially oblique to the plane passing through the base while the tool is in a closed position, a pin mounted on the second surface of the first arm, and an opening through the second arm that receives the pin. A portion of the angled first tip and a portion of the angled second tip mate when the tool is in a closed position such that the pin engages the opening. The dental tool further includes a first pressure portion on the first surface of the first arm, a second pressure portion on the first surface of the second arm, a plurality of indentations on the first pressure portion and the second pressure portion, a first mating portion on the second surface of the first arm and opposite the first pressure portion, and a second mating portion on the second surface of the second arm and opposite the second pressure portion. The second mating portion is contiguous with the first mating portion when a maximum pressure is applied to the first pressure portion and the second pressure portion. The first tip and the second tip grasp an object having a substantially planar surface such that a line passing through a center of the object is perpendicular to the plane.

BRIEF DESCRIPTION OF THE DRAWINGS

The accompanying drawings, which are incorporated herein and constitute part of this specification, illustrate the presently preferred embodiment of the invention, and, together with the general description given above and the detailed description given below, serve to explain the features of the invention.

DETAILED DESCRIPTION OF THE PREFERRED EMBODIMENTS

Reference will now be made in detail to the preferred embodiments of the present invention, examples of which are illustrated in the accompanying drawings. It is to be understood that the Figures and descriptions of the present invention included herein illustrate and describe elements that are of particular relevance to the present invention, while eliminating, for purposes of clarity, other elements found in typical dental instruments.

Figure 1:
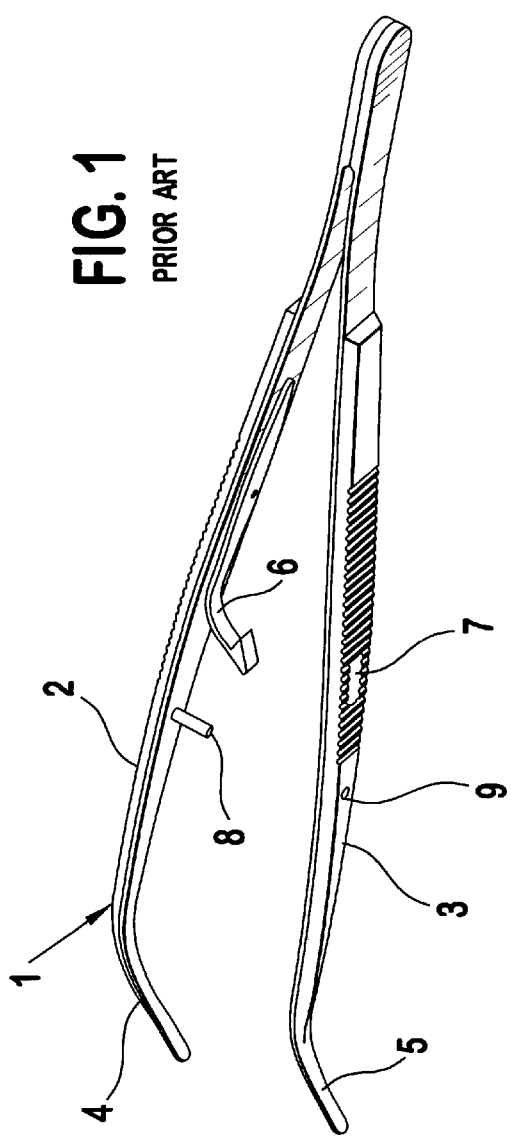
FIG. 1 is a side elevational view of a prior art dental instrument.
Figure 2:
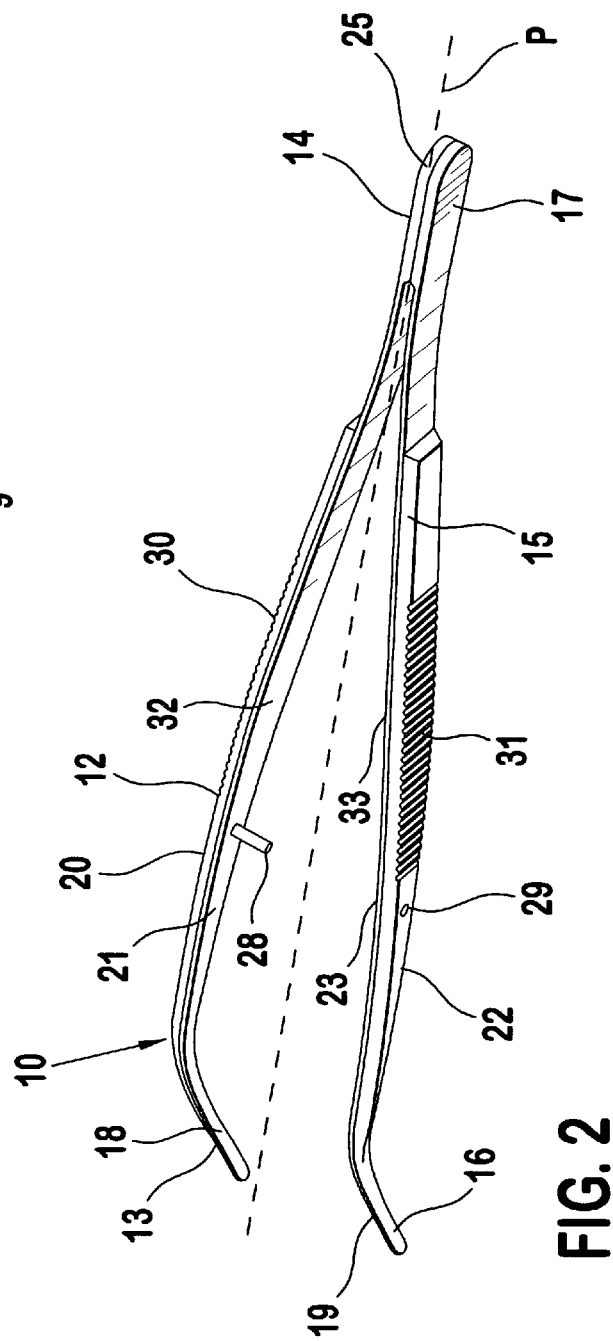
FIG. 2 is a side elevational view of the preferred embodiment of the grasping tool of the present invention.

FIG. 1 illustrates the grasping tool, or dental tool, 10 in an open position. The grasping tool 10, which may be formed of metal or any other suitable material, has a first arm 12 with a first tip 13, which is preferably angled, and a first end 14 opposite the first tip 13 and a second arm 15 with a second tip 16, which is preferably angled, and a second end 17 opposite the second tip 16. In the preferred embodiment, the first tip 13 and the second tip 16 have substantially planar surfaces 18 and 19, respectively. The first arm 12 has a first surface 20 and a second surface 21 opposite the first surface 12. The second arm 15 has a first surface 22 and a second surface 23 opposite the first surface 22. The second surface 21 of the first arm 12 faces the second surface 23 of the second arm 15. The second end 17 is affixed to the first end 14 to form a base 25, and a plane P passes through the base 25 between the first arm 12 and the second arm 15. The base may be formed from a weld or a screw passing through the first end 14 and the second end 17. A pin 28 is mounted on the second surface 21 of the first arm 12, and an opening 29 through the second arm 15 receives the pin 28.

The grasping tool 10 also includes a first pressure portion 30 on the first surface 20 of the first arm 12 and a second pressure portion 31 on the first surface 22 of the second arm 15. In the preferred embodiment, the first pressure portion 30 and the second pressure portion 31 have indentations. A first mating portion 32 is located on the second surface 21 of the first arm 12 and opposite the first pressure portion 30, and a second mating portion 33 is located on the second surface 23 of the second arm 15 and opposite the second pressure portion 31.

Figure 3:
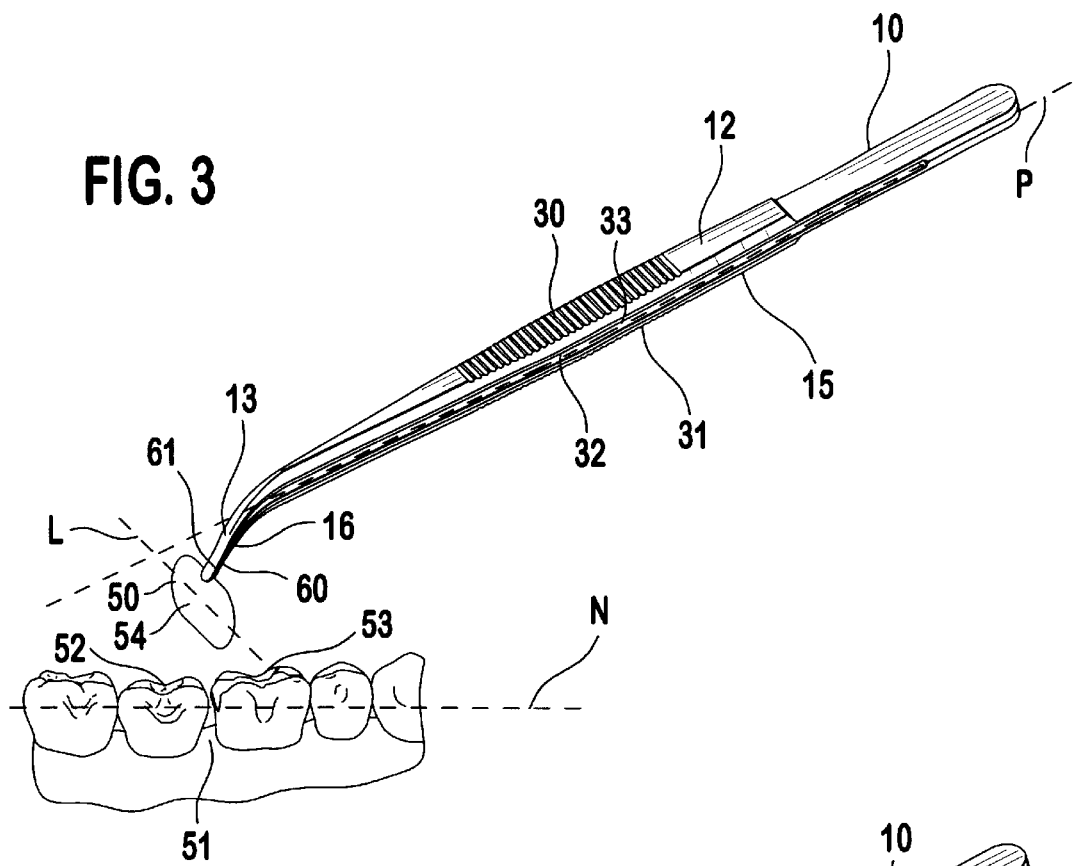
FIG. 3 is a top elevational view of the grasping tool of FIG. 2 inserting an object between a pair of teeth.

Preferably, the grasping tool 10 is used to place an object 50 into a channel 51 between a pair of teeth 52 and 53, as shown in FIG. 3. The object 50 has a substantially planar surface 54 and preferably, fits into the channel 51. In the preferred embodiment, the object 50 is a sectional matrix, or containment device, that prevents the flow of filling material while at least one of the teeth 52 and 53 are being repaired, or filled. It should be understood that the grasping tool 10 may be used to pick up any type of object. It should further be understood that the grasping tool 10 may be used to move objects to receiving articles other than a channel between teeth. To place the object 50 into the channel 51, in the preferred embodiment, the grasping tool 10 is picked up and held, preferably by two fingers, on the first pressure portion 30 and the second pressure portion 31. To grasp the object 50, pressure is applied to the first pressure portion 30 and the second pressure portion 31, simultaneously. In the preferred embodiment, the first arm 12 and the second arm 15 are moved at substantially the same distance toward the plane P, and the pin 28 is inserted into the opening 29 to align the first arm 12 with the second arm 15. The object 50 is, preferably, held between the first tip 13 and the second tip 16 such that a line L passing through the center of the object 50 is perpendicular to the plane P.

Once the object 50 is grasped, or picked up, the grasping tool 10 is in a closed position. While in a closed position, the first tip 13 and the second tip 16 are substantially oblique to the plane P, and a portion 61 of the first tip 13 and a portion 60 of the second tip 16 mate. The second mating portion 33 will be contiguous with the first mating portion 32 when a maximum pressure is applied to the first pressure portion 30 and the second pressure portion 31. The grasping tool 10 is, preferably, placed inside a mouth and moved toward the channel 51. In the preferred embodiment, the grasping tool 10 enters the mouth such that the first arm 12 and the second arm 15 are substantially oblique to a line N passing through centers of the teeth 52 and 53.

Figure 4:
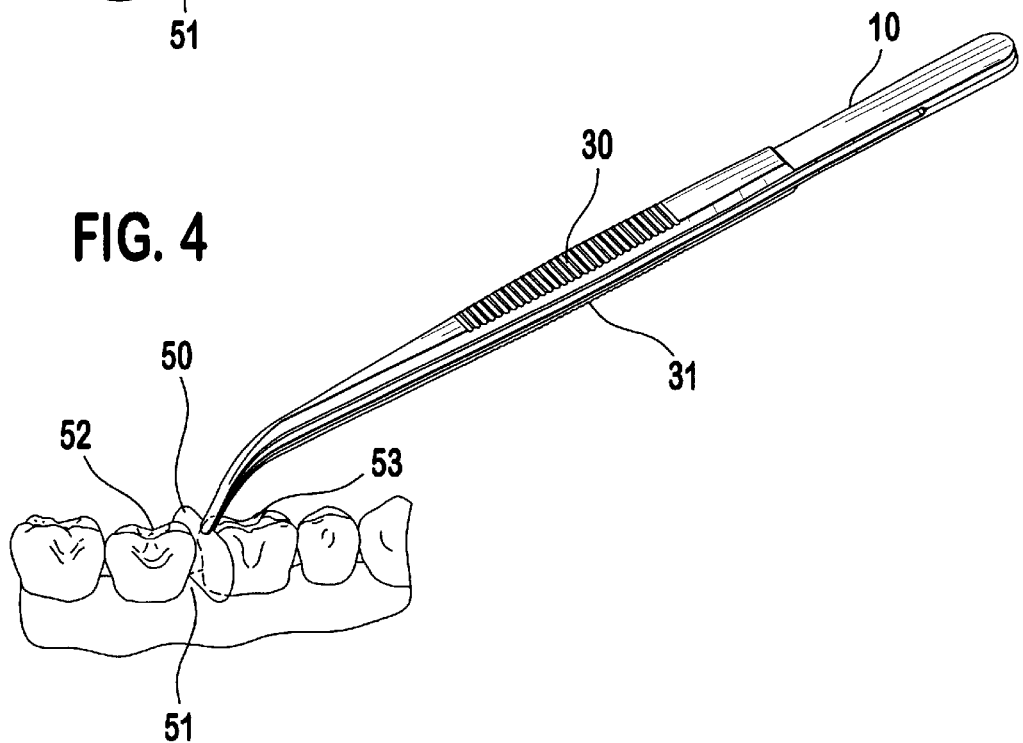
FIG. 4 is a top elevational view of the grasping tool of FIG. 1 with the object located between the pair of teeth.

As shown in FIG. 4, the object 50 is inserted into the channel 51 between the teeth 52 and 53. The grasping tool 10 allows for easy mobility inside the mouth and in particular, toward the back of the mouth. As such, a patient may experience less discomfort. The pressure from the first pressure potion 30 and the second pressure portion 31 is released to free the object 50 from the grasping tool 10. Once the object 50 is inserted, it may be dislodged, or removed, by applying pressure on the first pressure portion 30 and the second pressure portion 31, simultaneously, to grasp the object 50, removing the object 50 from the channel 51, moving the grasping tool 10 and the object 50 away from the channel 51, and releasing the pressure from the first pressure portion 30 and the second pressure portion 31 to free the object 50 from the grasping tool 10.

While the invention has been described in detail and with reference to specific features, it will be apparent to one skilled in the art that various changes and modifications can be made therein without departing from the spirit and scope of the invention. For example, the pressure portions may include a gripping surface, rather than indentations. It is intended that the present invention cover the modifications and variations of this invention provided they come within the scope of the appended claims and their equivalents.

What I claim is:

1. A method of placing an object having a substantially planar surface into a channel between a pair of teeth comprising:

providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, the first end affixed to the second end to form a base, the first tip and the second tip substantially oblique to a plane passing through the base, the first surface of the first arm being opposite the first surface of the second arm;

applying pressure on the first pressure portion and the second pressure portion simultaneously to grasp the object;

moving the dental tool and the object toward the channel;

inserting the object into the channel; and releasing the pressure from the first pressure portion and the second pressure portion to free the object from the dental tool.

2. The method of claim 1, the first tip and second tip being bent at a common angle, wherein the applying comprises:

grasping the object with the first tip and the second tip.

3. The method of claim 1 wherein the moving comprises:

entering a mouth such that the first arm and the second arm are substantially oblique to a line passing through centers of the pair of teeth and the channel.

4. The method of claim 1 further comprising:

inserting the pin into the opening to align the first arm with the second arm.

5. The method of claim 1 wherein the applying comprises:

moving the first arm and the second arm at substantially the same distance toward the plane.

6. The method of claim 1 wherein the applying comprises:

grasping the object such that a line passing through a center of the object is perpendicular to the plane.

7. The method of claim 1 wherein the applying comprises:

grasping the object such that a first line passing through a center the object is perpendicular to a second line passing through a center of the first and second arms.

8. The method of claim 1 wherein the applying comprises:

exerting a maximum pressure on the first pressure portion and the second pressure portion; and contacting a first mating portion of the first arm with a second mating portion of the second arm such that the first mating portion is contiguous with the second mating portion, the first mating portion being opposite the first pressure portion and the second mating portion being opposite the second pressure portion.

9. The method of claim 1 further comprising:

picking up the dental tool; and holding the dental tool at the first pressure portion and the second pressure portion.

10. The method of claim 1 further comprising:

providing a plurality of indentations on the first pressure portion and the second pressure portion.

11. A method of placing an object having a substantially planar surface into a channel between a pair of teeth comprising:

providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, the first end affixed to the second end to form a base, the first tip and the second tip substantially oblique to a plane passing through the base, the first surface of the first arm being opposite the first surface of the second arm;

picking up the dental tool;

holding the dental tool at the first pressure portion and the second pressure portion;

applying pressure on the first pressure portion and the second pressure portion simultaneously;

moving the first arm and the second arm at substantially the same distance toward the plane;

inserting the pin into the opening to align the first arm with the second arm;

grasping the object with the first tip and the second tip such that a line passing through a center of the object is perpendicular to the plane;

moving the dental tool and the object toward the channel;

entering a mouth such that the first arm and the second arm align are substantially oblique to a line passing through each center of the pair of teeth and the channel;

inserting the object into the channel; and releasing the pressure from the first pressure portion and the second pressure portion to free the object from the dental tool.

12. A method of dislodging an object having a substantially planar surface from a channel between a pair of teeth comprising:

providing a dental tool having a first arm with a first tip and a first end, a first pressure portion on a first surface, and a pin mounted on a second surface opposite the first surface and a second arm with a second tip and a second end, a second pressure portion on a first surface and an opening that receives the pin, the first end affixed to the second end to form a base, the first tip and the second tip substantially oblique to a plane passing through the base, the first surface of the first arm being opposite the first surface of the second arm;

applying pressure on the first pressure portion and the second pressure portion simultaneously to grasp the object;

removing the object from the channel;

moving the dental tool and the object away from the channel; and releasing the pressure from the first pressure portion and the second pressure portion to free the object from the dental tool.

* * * * *